United States Patent [19]

Holly et al.

[11] Patent Number: 5,380,303
[45] Date of Patent: Jan. 10, 1995

[54] METHOD FOR USING AN ANTIMICROBIAL AGENT FOR OPHTHALMIC FORMULATIONS

[75] Inventors: Frank J. Holly, 301 York Ave., Lubbock, Tex. 79416; Stephen R. Tonge, Birmingham, England

[73] Assignee: Frank J. Holly, Lubbock, Tex.

[21] Appl. No.: 112,942

[22] Filed: Aug. 30, 1993

Related U.S. Application Data

[63] Continuation of Ser. No. 891,425, May 29, 1992, Pat. No. 5,300,296, which is a continuation-in-part of Ser. No. 432,171, Nov. 6, 1989, abandoned.

[51] Int. Cl.⁶ .............................................. A61M 35/00
[52] U.S. Cl. ................................. 604/290; 604/294; 424/427; 424/78.31; 514/642; 514/839; 514/912; 514/913; 514/914; 523/122
[58] Field of Search ................ 424/78.31, 427; 514/642, 912, 913, 914, 839, 950; 523/122; 422/36; 604/289, 290, 294

[56] References Cited

U.S. PATENT DOCUMENTS

| | | | |
|---|---|---|---|
| 4,025,617 | 5/1977 | Green et al. | 424/78 |
| 4,171,377 | 10/1979 | Green et al. | 424/319 |
| 4,201,706 | 5/1980 | Trngu et al. | 424/78 |
| 4,304,894 | 12/1981 | Andrew et al. | 526/310 |
| 4,407,791 | 10/1983 | Stare | 424/80 |
| 4,548,812 | 10/1985 | Foley | 424/78 |
| 4,791,063 | 12/1988 | Hou et al. | 435/243 |

*Primary Examiner*—Randall L. Green
*Assistant Examiner*—Mary Beth O. Jones
*Attorney, Agent, or Firm*—Henri J. A. Charmasson; John D. Buchaca

[57] ABSTRACT

A disinfectant or preservative composition particularly adapted for use in ophthalmic preparations such as contact lens disinfecting, cleaning, cushioning, wetting, soaking and reconditioning solutions and additionally in topical medications and tear substitutes, which uses a hydrophilic polymeric antimicrobial agent, namely poly[oxyethylene(dimethylimino) (ethylene dimethylimino)ethylene dichloride] with additional agents including EDTA and alkali salts thereof and a boric acid/borate buffer system.

6 Claims, No Drawings

METHOD FOR USING AN ANTIMICROBIAL AGENT FOR OPHTHALMIC FORMULATIONS

PRIOR APPLICATION

This application is a continuation of co-pending application Ser. No. 07/891,425 filed May 29, 1992, now U.S. Pat. No. 5,300,296, which is a continuation-in-part of Ser. No. 07/432,171 filed Nov. 6, 1989, now abandoned.

FIELD OF INVENTION

This invention relates to an ophthalmic disinfecting and preserving composition. More particularly, this invention relates to the disinfection of contact lenses especially soft hydrogel lenses and to preserving ophthalmic formulations such as aqueous solutions, suspensions, and ointments, especially those used in the treatment of ocular diseases, including the dry eye syndrome, in wetting and cushioning of contact lenses, and in the cleaning, cushioning, and reconditioning of contact lenses.

BACKGROUND OF THE INVENTION

Compounds used to disinfect ocular prostheses such as contact lenses or employed to preserve ophthalmic formulations designed to be applied directly to the eye or to objects which are in direct contact with the eyes, must be non-irritating and free of any detrimental side effects. Yet, they must be sufficiently effective against bacteria and fungi to ensure the sterility of such prostheses or guarantee a reasonable shelf-life of the ophthalmic formulations and thereby prevent infections. The inherent conflict between antimicrobial efficiency on the one hand, and non-irritancy on the other has lead to compromises. The conventional microbial agents which can be found in ophthalmic formulations comprise:

Benzalkonium chloride, benzethonium chloride, benzyl alcohol, chlorobutanol, chlorhexidine digluconate or diacetate, methyl and propyl hydroxybenzoate (parabens), phenylethyl alcohol, phenylmercuric acetate or nitrate, sorbic acid, and thimerosal.

Presently there are two polymeric preservatives used in ophthalmic products under the trademarks of "Polyquad" and "Dymed". "Polyquad". Polyquad is alpha-4[1-tris(2-hydroxyethyl) ammonium chloride-2-dibutenyl] poly[1-dimethyl ammonium chloride-2-dibutenyl]-ω-tris (2-hydroxyethyl) ammonium chloride. Dymed brand is poly[aminopropyl-bis(biguanide)] or poly[hexamethylene-bis(biguanide)] and has a lower molecular weight, and hence, is a considerably smaller molecule. Although non-irritating, neither compound is effectively fungicidal at the concentrations employed in ophthalmic formulations and both compounds require additional agents to achieve such an effect.

Some attributes of a disinfectant/preservative, which would be very desirable from an ophthalmic point of view, are:

1) Bactericidal and fungicidal activity at concentration levels which are much lower than those likely to cause damage to mammalian cells, i.e. selective toxicity.
2) Nonirritant to the ocular surface upon topical application.
3) Innocuous toward corneal epithelial or endothelial cells.
4) Effective in the physiological pH range, i.e. pH 6–8.
5) Not acting as a sensitizing agent to ocular tissues unlike thimerosal and chlorhexidine.
6) Readily soluble in aqueous solution.
7) Chemically and thermally stable in aqueous solution and able to withstand autoclaving (20 minutes at 120 degrees centigrade).
8) Possessing prolonged chemical stability in aqueous solution at physiological pH's (acceptable shelf-life).
9) Not absorbed into the polymer matrix of hydrogel lenses thereby not accumulating within the matrix of the lens nor leaching into the ocular tissues upon application of the lens to the eye.
10) Not adsorbed adversely onto the surface of the contact lenses, so as to diminish the water wettability of such lenses, nor increases the water/lens interfacial tension appreciably and thereby reduce lens ocular compatibility and perceived in-eye comfort.
11) Not interfering with the solubility or other properties of the components of the ocular formulation to be preserved such as contact lens wetting, film forming, and viscosity-modifying agents or therapeutic agents.
12) Neither absorbed into nor adsorbed onto the polymers used in the construction of eye-dropper containers (bottles).
13) Not absorbed systemically, i.e. by the bodily organs via the circulatory system.
14) Free of toxic heavy metal ions which may act as cumulative poisons in the body.

It is important to note here that none of the earlier listed presently available preservatives fulfill all of the above criteria especially those listed as items 9 and 10.

The monomeric antibacterial agents listed earlier cannot be added to ophthalmic formulations likely to be used by patients who wear hydrogel contact lenses because the small molecular size of these agents enable them to penetrate pores of hydrogels, the polymeric matrices of the hydrogel materials. The antimicrobial agent accumulated within the lens matrix would eventually leach into the tear film upon application of the lens to the eye. The pore size in poly(hydroxyethylmethacrylate) [poly(HEMA)] gels used in the fabrication of hydrogel lenses is approximately 30–50 Angstroms, as reported in Hydrogels in Medicine and Pharmacy, Vol. II, Polymers. Ed. Peppas, N. K., CRC Press, Inc. To prevent the absorption of antimicrobial agents into such lenses the use of polymeric anti-microbial agents has been suggested namely by Andrews, J. K. in U.S. Pat. No. 4,304,894 and Stark, R. L. in U.S. Pat. No. 4,407,791.

Until recently, virtually all of the commercially available hydrogel lenses were fabricated from neutral polymeric materials such as poly(HEMA). However, the introduction of disposable lenses, such as those sold under the trademark name "Acuvue" by Johnson and Johnson, Inc., has led to the reintroduction and widespread use of a contact lens material fabricated by the anionic Etafilcon A and containing methylmethacrylic acid groups. Such lenses are not ideally suited for use with ophthalmic solutions containing polyquaternary ammonium antimicrobial agents, since the latter agents react electrostatically with the surfaces of such materials.

Clinical impressions suggest that such polyquaternary ammonium disinfectant solutions do indeed adsorb to the surfaces of certain soft lens materials, especially anionic materials, and cause ocular discomfort. It is essential for the lens to retain its wettability and low interfacial tension against tear, and allow a continuous film of tear fluid covering, in order to remain acceptable to the contact lens wearer.

Interaction between the positively charged hydrophilic polyquaternary ammonium groups of anti-bacterials and anionic lenses causes the lens surface to become covered with a layer of hydrophobic polymer and may lead to dewetting. Hence, agents which act to lower the critical surface tension of a contact lens should be avoided when formulating ophthalmic products used for disinfecting, cleaning, cushioning, and reconditioning contact lenses or in ophthalmic medications likely to be used in patients who wear contact lenses, e.g. artificial tears and vasocon-strictors.

Ellis, E. J. et al U.S. Pat. Nos. 4,168,112 and 4,436,730 disclose the treatment of hard and soft contact lens materials bearing a surface electric charge with a solution comprising hydrophilic polymers possessing an opposite charge in order to form a layer of hydrophilic polyelectrolyte complex and enhance surface wettability. These patents teach the use of polyionene polymers and cationic polyethylene imine to that effect. However, they do not teach the use of the polyionene co-polymer, or the use of copolymers formed from cationic and nonionic monomeric components, nor do they teach dimethylimino ethylene as a cationic monomer, either as part of the homo or co-polymer as will be disclosed below.

The results of comparative tests set out in Table IV below indicate that the polyionene present in Polyquad does not facilitate the wetting of contact lens surfaces. Therefore, the disclosure by Ellis et al that polyionenes as a group may be considered as useful agents for facilitating the wetting of anionically charged contact lens matrices including soft lenses is not supported. We found that only particular polyionenes possess the ability to wet the surface of anionically charged contact lens surfaces well. It is never obvious from the molecular structure which polyionene is likely to possess this coveted property. Structure-activity relationship of copolymers cannot be directly-inferred from the functional properties of their monomeric constituents due to the potential for multiple orientations within such large molecules. This can only be defined experimentally. Hence, it is not evident, and indeed undefined, in the disclosure of Ellis which polyionenes are capable for facilitating the wetting of contact lenses.

The homopolymer of ethylene oxide is cited as a means of wetting anionic surfaces by Ellis et al in U.S. Pat. No. 4,321,261 but only by means of hydrogen bonding and not, as we found, as part of a copolymer combined with a cationic monomer where the molecular binding to lens occurs electrostatically.

The disclosures made by Ellis et al are solely concerned with the use of polycationic polymers, including polyquaternary polymers and polyionenes as a means of enhancing the wettability of contact lenses and do not suggest that they may act additionally as antimicrobial agents in ophthalmic solutions such as contact lens care solutions. The presence of accepted ophthalmic preservative agents, such as benzalkonium chloride, in the formulations shown in the examples of the cited patents of Ellis et al further indicate that said invention relates solely to a means of wetting contact lenses. Furthermore, it is not recognized by the inventors that certain polyquaternary agents such as benzalkonium chloride at low concentrations may act as dewetting agents, i.e. they convey to the solid surface hydrophobic properties.

In comparison we have found that the polyionene in certain compositions surprisingly possesses both antimicrobial properties and an ability to enhance rather than diminish the wetting characteristics of contact lenses especially the anionically charged lens surfaces, and thus offers unique advantages over the previously listed disinfectants and preservatives which are conventionally used in ophthalmic formulations.

Although, Stark, R. L. expressly teaches the use of a polyionene antimicrobial agent for disinfecting contact lenses and preserving ophthalmic solutions including ophthalmic medicaments in U.S. Pat. No. 4,407,791, ("Polyquad brand") and Ogunbiyi et al expressly teach the use of a polymeric biguanide as a method of disinfecting contact lenses in U.S. Pat. No. 4,836,986 ("Dymed"), neither patent teaches or suggests the use of the polymer described in the present invention.

While there may be many industrial and even pharmaceutical disinfectants and preservatives available, their suitability to ophthalmic applications is never obvious and their potential must be first recognized, then carefully formulated and clinically tested to achieve a satisfactory balance of efficacy, safety and contact lens compatibility.

SUMMARY OF THE INVENTION

Accordingly, there has been a need for improved disinfecting and preserving solutions which maintain contact lens surface wettability, and retard rather than promote surface spoilage of these lenses.

It has now been found that an aqueous solution of a particular polymeric quaternary ammonium salt provides an anti-microbial solution suitable for use as a disinfecting solution for contact lenses as well as a preservative vehicle for ophthalmic solutions including contact lens care solutions and ophthalmic medicaments. The solution can be considered an improvement over similar polymeric antimicrobial formulations in that it retains and even improves the surface wettability of the contact lenses especially those bearing an anionic charge. The particular polymeric quaternary ammonium salt is a copolymer of ethylene oxide and dimethylimino ethylene in a 1:2 molecular ratio.

This invention is characterized by the use of an industrial polymeric antimicrobial agent: Poly[oxyethylene(-dimethylimino)-ethylene-(dimethylimino)ethylene dichloride] in a pharmaceutical preparation in combination with a buffer and metal ion chelating agent for application to ophthalmic solutions for disinfecting contact lenses and preserving ocular solutions used to treat contact lenses and ocular disease.

BRIEF DESCRIPTION OF THE PREFERRED EMBODIMENT OF THE INVENTION

This invention is based on the use for ophthalmic purposes of a polymeric antimicrobial, code-named NPX.

NPX is a dihalogenated polyionene, poly[oxyethylene-(dimethylimino)-ethylene-(dimethylimino)-ethylene dichloride], in which the quaternary nitrogens form an integral part of the polymeric backbone. Chemically it may be considered to be a copolymer of ethylene oxide and dimethyl ethylene-imine in a 1:2 molecular ratio having the following structure:

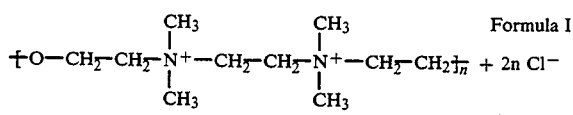

Formula I

The product sold under the trademark "WSCP" and manufactured by Buckman Laboratories, Memphis, Tenn., is such a compound, and is used to sanitize water in swimming pools and in water-based cooling systems in the concentration range 0.0002–0.002% weight per volume.

NPX is a broad spectrum polycationic antimicrobial effective against both gram-positive and gram-negative bacteria, certain fungi (yeasts) and algae at concentration levels as low as 0.0002%. In vitro microbiological challenge tests (see Table I) indicate that NPX at concentrations ranging from 0.001% to 0.024% by weight is completely effective against bacteria (*S. aureus, P. aeruginosa* and *E. coli*) and yeast (*C. albicans*).

The average molecular extended chain length of NPX is 181 521 (range 103–620 Å) equivalent to some 13.5 base units (range 7.7–46.3), and represented by the suffix 'n' in the chemical structure shown above as Formula I with a corresponding number average molecular weight of 3,500 daltons (range 2,000–12,000). Thus the molecule is smaller than that of "Polyquad" of Alcon Laboratories, which has an average molecular size of 225 Å.

TABLE I

Antimicrobial Efficacy of NPX at Various Concentrations

| TYPE OF ORGANISM | SPECIES TESTED | INOCULUM cell/g | Cell count after one week in different concentrations of NPX | | |
|---|---|---|---|---|---|
| | | | 0.001% | 0.0048% | 0.024% |
| Yeast | *Candida albicans* | $3.8 \times 10^5$ | 0 | 0 | 0 |
| Mold | *Aspergillus niger* | $2.2 \times 10^5$ | $5.6 \times 10^4$ | $7.4 \times 10^4$ | $7.8 \times 10^4$ |
| Bacteria | *Escherichia coli* | $1.1 \times 10^6$ | 0 | 0 | 0 |
| Bacteria | *Pseudononas aerigunosa* | $6.8 \times 10^5$ | 0 | 0 | 0 |
| Bacteria | *Staphylococcus aureus* | $1.2 \times 10^6$ | 0 | 0 | 0 |

The molecular size of polymeric antibacterial agents is crucial when treating hydrogel materials such as soft contact lenses. In order to prevent accumulation of the antibacterial agent within the polymer matrix of the lens, such agents have to be larger than the average pore size of the gel ranging between 30 and 50 Å. However, the antimicrobial efficacy of polymeric agents appears to be inversely related to their molecular size. Hence, there appears to exist an optimal molecular size; larger than the hydrogel pore size but not so large as to result in a significant loss of antimicrobial activity.

NPX exhibits just such an optimal molecular size, larger than the gel pore size but smaller than the molecular size of the polyquad brand. Consequently, as Table III shows, NPX is a more potent anti-microbial than "Polyquad" when tested in vitro against *Aspergillus niger* according to the test procedures described in USP XXI. NPX at 0.001% by weight, combined with 0.08% by weight of the tetrasodium salt of ethylenediaminetetraacetic acid (EDTA) and buffered to pH 7 with a borate buffer system, reduces the initial concentration of Aspergillus niger by one thousand-fold after seven days. On the other hand, "Polyquad" 0.001% by weight combined with 0.05% by weight disodium EDTA buffered to pH 7.5 only reduces the concentration of *Aspergillus niger* by a hundred-fold after fourteen days.

However, similarly to other polyquaternary compounds, e.g. Polyquad brand and to monomeric and polymeric biguanides, e.g. chlorhexidine digluconate and "Dymed", respectively, NPX does not kill molds but only retards their growth (fungistatic but not fungicidal). When we combined an aqueous solution of 0.01% by weight NPX with 0.08% by weight of tetrasodium EDTA and buffered the solution with 0.35% by weight boric acid and 0.02% by weight sodium borate, the antifungal properties were greatly enhanced, such that the NPX formulation described meets the criteria outlined in the UPS XXI Antimicrobial Preservative Effectiveness Test. However, even this improved solution fails to completely eliminate the fungal inoculum (see Table II). It should be noted that U.S. Pat. No. 4,361,548 to Smith et al expressly teaches the addition of enhancers such as 0.5% by weight EDTA to a dimethyldiallylammonium chloride homopolymer solution for the purpose of disinfecting contact lenses, while U.S. Pat. No. 4,836,986 to Ogunbiyi et al expressly teaches that the addition of alkali salts of EDTA combined with a borate buffer system enhances the antifungal efficacy of solutions containing the "Dymed" of disinfectant.

As stated above, antimicrobial agents used in ophthalmic solutions must be completely nonirritant when instilled into the eye.

In vivo studies conducted in rabbit and human eyes have shown that NPX

TABLE II

Antifungal Efficacy of NPX in the Presence of Borate Buffer and Tetrasodium Salt of EDTA

| TYPE OF ORGANISM | SPECIES TESTED | INOCULUM Cell/g | CELL COUNT AFTER ONE WEEK AT 0.01% CONCENTRATION OF NPX |
|---|---|---|---|
| Mold | *Aspergillus Niger* | $5.3 \times 10^5$ | 33 | in an aqueous solution does not irritate eyes when used in concentrations up to 1 percent by weight. Acute repeated exposure studies in six eyes of human volunteers, compared to physiologic saline, demonstrated that NPX only causes minor epithelial damage detectable by vital staining subsequent to the instillation of a drop every ten minutes for three hours. At such an exaggerated exposure, even physiologic saline commences to cause some epithelial damage (see Table III).

Although 0.01% NPX has previously been used to sanitize swimming pools at levels of 0.001%, unexpectedly, our observations indicate that when formulated in an ophthalmic solution with excipients such as those described herein, it is nonirritant to ocular tissues when applied in concentrations up to 1% by weight. In comparison with an ophthalmic formulation containing 0.00001% by weight of the antimicrobial polyionene: poly(methyldiallyl ammonium chloride) as described in U.S. Pat. No. 4,361,548 to Smith et al, according to disclosures made in U.S. Pat. No. 4,758,595 to Ogunbiyi et al causes an unacceptable degree of ocular irritation in some patients. The polymeric biguanide antimicrobial disclosed in the last patent also causes an unacceptable amount of corneal staining when instilled in human eyes at levels of 0.0005% by weight or greater. In comparison, NPX appears to be far less irritant to the ocular tissues.

Besides possessing potent antimicrobial activity and being

TABLE III

Acute Ocular Toxicity Test Results of 0.10% NPX

| | | | | EPITHELIAL INTEGRITY AFTER INSTILLATION OF "N" DROPS | | |
|---|---|---|---|---|---|---|
| SUB-JECT | SEX/AGE | EYE | N | Tear Film Debris | Vital Staining | Conjunctival Injection |
| FJH | M/54 | OD/OS | 6 | 0/0 | 0/0 | 0/0 |
| | | | 12 | 0/0 | 0/0 | 0/0 |
| | | | 18 | 0/0 | 0/0 | 0/0 |
| | | | 18* | 0/0 | 0.5/0 | 0/0 |
| TFH | M/19 | OD/OS | 6 | 0/0 | 0/0 | 0/0 |
| | | | 12 | 0/0 | 0/0 | 0/0 |
| | | | 18 | 0/0 | 1/0.5 | 0/0 |
| | | | 18* | 0/0 | 0/0 | 0/0 |
| SFT | M/30 | OD/OS | 6 | 0/0 | 0/0 | 0/0 |
| | | | 12 | 0/0 | 0/0 | 0/0 |
| | | | 18 | 0/0 | 0.5/0 | 0/0 |
| | | | 18* | 0/0 | 0.5/0 | 0/0 |

*vital stain used is the irritating Rose bengal instead of the more customary fluorescein, sodum salt.
Remark: Right eye [OD]: saline preserved with NPX; Left eye [OS]: unpreserved saline.

nonirritant to ocular tissues when formulated as an ophthalmic solution such as described herein, it has been shown by in vitro studies of surface wettability of solid test surfaces such as the nonpolar polyethylene and the polar poly(methyl methacrylate) surfaces, that solutions of NPX make the solid surface more wettable as shown by the low value of the receding contact angle. Both the adsorption of Dymed brand and the Polyquad brand exhibited a significantly higher receding contact angle values. Table IV shows the results of advancing and receding contact angles of antimicrobial containing solutions determined on glossy poly-ethylene surface and glossy poly(methyl methacrylate) surface. These in vitro measurements clearly indicate that the adsorption of NPX makes even hydrophobic surfaces more hydrophilic than either "Dymed" or "Polyquad" antimicrobials [cf. F. J. Holly: "Novel methods of studying polymer surfaces by employing contact angle goniometry". In PHYSICOCHEMICAL ASPECTS OF POLYMER SURFACES, Ed. by K. L. Mittal, Plenum, 1983, pp 141–154].

The relatively invariant advancing contact angle values indicate that the spreading coefficient of the solutions is little affected by these substances. However, the low receding contact angles indicate a higher degree of water wettability and also a greater degree of aqueous film stability over such a surface due to solute adsorption. Such a surface is expected to be more biocompatible.

TABLE IV

Water Wettability of a Nonpolar Polymeric Solid and a Polar Polymeric Solid Surface as Affected by the Adsorption of NPX, Polyquad, and Dymed Antimicrobials

| | POLYETHYLENE | | POLY(METHYL METHACRYLATE) | |
|---|---|---|---|---|
| SOLUTION | ADVANCING* | RECEDING* | ADVANCING* | RECEDING* |
| WATER | 92 ± 2° | 90 ± 2° | 82 ± 3° | 39 ± 2° |
| 0.001% NPX | 91 ± 3° | 26 ± 2° | 82 ± 3° | 12 ± 2° |
| 0.001% Dymed | 92 ± 3° | 43 ± 3° | 82 ± 2° | 32 ± 3° |
| 0.001% "Polyquad" | 86 ± 3° | 39 ± 3° | 81 ± 3° | 24 ± 4° |

*contact angle values formed by a sessile drop of the solution resting on the solid indicated above Hence, the particular combination of favorable properties of the NPX containing ophthalmic composition cited in the present invention appear unexpected and quite unique in exhibiting potent antimicrobial activity combined with extremely low ocular irritancy, even when used in concentrations up to 1% by weight. In addition, NPX, rather than hindering, actually facilitates wetting of model surfaces both nonpolar and polar (the range would include hydrogel contact lens surfaces) and, as a consequence, improves the ocular comfort and safety of patients wearing lenses treated with formulations defined herein.

Formulations from examples I to III serve as illustrations of the formulations that can be used to disinfect contact lenses and do not purport to be wholly definitive as to the conditions and scope of this invention. Formulations from examples II–V also serve as illustrations of formulations preserved with NPX combined with additional excipients as described herein and used for treating contact lenses either prior to insertion into the eye or by direct application to contact lenses in situ.

The components of the formulations may also optionally include other water-soluble polymers, inorganic electrolytes, and other small molecular weight substances to obtain desired characteristics. Water-soluble polymers may be added as supplementary wetting agents, film-forming agents, and viscosity modifiers. Some of the wetting agents possess both film-forming and viscosity modifying properties. Those agents possessing wetting and film-forming properties may be selected from, but are not limited to, nonionic polymeric surfactants used at concentrations ranging from 0.02% to 4.5% by weight, including poloxamers such as those manufactured by the BASF Wyandotte Corporation under the trademark "Pluronic", e.g. grade F68, or polyoxyethylene sorbitan esters such as those manufactured by ICI Americas, Inc., under the trademark "Tween", e.g. grade 80. Other agents possess viscosity-modifying properties in addition to wetting and film-forming properties and these agents may be used to form part of the present invention. The latter agents include, but are not limited to substituted cellulose ethers such as hydroxypropylmethyl or hydroxypropylethyl cellulose used in amounts from 0.1% to 0.5% by weight and manufactured by Dow Chemical Company under the trade names "Methocel" and "Ethocel", povidone used at 0.1–5% by weight and manufactured by GAF Chemicals Corporation under the tradename "PVP K30" and acrylic copolymers used from 0.1% to 0.5% by weight and manufactured by Th. Goldschmidt AG. under the tradename "Merquat".

The aqueous NPX-containing solutions cited in the examples I–III can be effectively used to disinfect contact lenses by any of the well recognized methods, such as cold disinfection, by soaking the lenses at room temperature for a period of 4–12 hours, or in thermal methods, by heating the lenses to 80 degrees centigrade in a thermal disinfecting unit containing the said disinfecting solution for a period of 10 minutes.

EXAMPLE I:
Contact Lens Disinfecting Solution

| | |
|---|---|
| NPX | 0.001% |
| Sodium chloride | 0.78% |
| Tetrasodium edetate | 0.08% |
| Boric acid | 0.35% |
| Sodium borate | 0.02% |
| Purified water | q.s. |
| pH | 6.0–8.0 |

EXAMPLE II
Preserved Saline/Contact Lens Rinsing, Soaking and Disinfecting Solution:

| | |
|---|---|
| NPX | 0.001% |
| Sodium chloride | 0.78% |
| Tetrasodium edetate | 0.08% |
| Boric acid | 0.35% |
| Sodium borate | 0.02% |
| Purified water | q.s. |
| pH | 6.0–8.0 |
| Potassium chloride | 0.6% |

EXAMPLE III:
Contact Lens Disinfecting, Wetting, Soaking, and Reconditioning Solution:

| | |
|---|---|
| NPX | 0.001% |
| Tetrasodium edetate | 0.12% |
| Hydroxypropylmethyl cellulose | 0.40% |
| Acrylic polymer | 0.50% |
| sodium chloride | 0.8% |
| boric acid | 0.35% |
| sodium borate | 0.02% |
| Tween 80 | 0.02% |
| Purified water | q.s. |
| pH | 7.0–8.0 |

EXAMPLE IV:
Contact Lens Cleaning Solution:

| | |
|---|---|
| NPX | 0.001% |
| Tetrasodium edetate | 0.12% |
| Pluronic F68 | 4.5% |
| Boric acid | 0.35% |
| Sodium borate | 0.02% |
| Purified water | q.s. |
| pH | 7.4 |

EXAMPLE V:
Lens Cushioning Solution:

| | |
|---|---|
| NPX | 0.001% |
| Tetrasodium edetate | 0.12% |
| Hydroxypropylethyl cellulose | 0.15% |
| Povidone | 0.50% |
| Sodium chloride | 0.85% |
| Boric acid | 0.35% |
| Sodium borate | 0.02% |
| Purified water | q.s. |
| pH | 7.0–8.0 |

This antimicrobial agent can also be used for the preservation of tear substitutes used in the treatment of the dry eye syndrome comprising the antimicrobial formulation of the present invention combined with additional salts to form a physiological balanced salt solution and additional wetting agents, film forming agents, and viscosity modifying agents such as those previously described.

In addition, the antimicrobial composition of the present invention can be used as a vehicle for preserving the active agents, e.g. drugs used in aqueous ophthalmic medicaments. The antimicrobial composition of the present invention can also be used to preserve ophthalmic suspensions and ointments, one example of each preparation is given.

The following drugs are quoted here as examples of ophthalmic drugs and are not intended to limit the scope of the invention. The medicaments are selected on the basis of diagnosis and indicated treatment for patients; dexamethasone for ocular inflammation, pilocarpine hydrochloride or beta-blockers for elevated intraocular pressure, and hydrochloric salts of ephedrine, phenylephrine, naphazoline, and tetrahydrozoline for injected eyes. Various anti-microbial agents effective in the treatment of mucous membranes infected with bacteria, fungi or viruses may also be preserved with the antimicrobial agent of the present invention. Antibacterials such as chloramphenicol, neomycin sulfate, bacitracin, gentamycin, sulfacetamide and polymixin B sulfate, antifungal agents such as amphotericin, and antiviral agents, such as acyclovir among others, may be preserved with NPX. For the treatment of ocular allergic reaction, antihistamines or mast-cell stabilizers could be included among the NPX-preserved formulae.

EXAMPLE VI:
Artificial Tear Formulation

| | |
|---|---|
| NPX | 0.001% |
| Tetrasodium edetate | 0.12% |
| Hydroxypropylmethyl cellulose | 0.20% |
| Sodium chloride | 0.77% |
| Potassium chloride | 0.11% |
| Calcium chloride dehydrate | 0.08% |
| Magnesium chloride $7H_2O$ | 0.02% |
| Boric acid | 0.35% |
| Sodium borate | 0.02% |
| Purified water | q.s. |
| pH | 7.5 |

EXAMPLE VII:
Anti-inflammatory Emulsion:

| | |
|---|---|
| Dexamethasone | 0.05% |
| NPX | 0.001% |
| Tetrasodium edetate | 0.12% |
| Substituted cellulose ether | 0.40% |
| Sodium chloride | 0.8% |
| Boric acid | 0.35% |
| Sodium borate | 0.02% |
| Tween 80 | 0.02% |
| Purified water | q.s. |
| pH | 7.2 |

EXAMPLE VIII:
Ocular Hypotensive Preparation:

| | |
|---|---|
| Pilocarpine HCl | 0.5% |
| NPX | 0.001% |
| Tetrasodium edetate | 0.12% |
| Substituted cellulose ether | 0.40% |
| Sodium chloride | 0.8% |
| Boric acid | 0.35% |
| Sodium borate | 0.02% |
| Purified water | q.s. |
| pH | 6.5 |

EXAMPLE IX:
Vaso-constrictor containing preparation:

| | |
|---|---|
| Phenylephrine HCl | 0.1% |
| NPX | 0.001% |
| Tetrasodium edetate | 0.12% |
| Substituted cellulose ether | 0.20% |
| Sodium chloride | 0.8% |
| Boric acid | 0.35% |
| Sodium borate | 0.02% |
| Purified water | q.s. |
| pH | 7.4 |

EXAMPLE X:
Anti-viral Ointment:

| | |
|---|---|
| Acyclovir | 3.0% |
| NPX | 0.001% |
| Tetrasodium edetate | 0.12% |
| Boric Acid | 0.35% |
| Sodium borate | 0.02% |
| Propylene glycol | 4.5% |
| White soft paraffin wax | 38% |

| | |
|---|---|
| Paraffin Oil | q.s. |

What is claimed is:

1. A method, for treating a patient eye affected by a syndrome, which comprises:
   applying to said eye, a topical medication comprising:
   an ophthalmically acceptable aqueous medium;
   an effective antimicrobial amount of poly[oxyethylene(dimethylimino)-ethylene-dimethylimino)-ethylene dichloride]copolymer in a 1:2 molecular from about 0.001 percent by weight to about 1.000 per cent by weight;
   an effective pH stabilizing amount of buffer;
   a metal ion chelating agent selected from a group consisting of ethylenediaminetetraacetic acid and alkali metal salts thereof; and
   applying a further preparation known to be effective against said syndrome.

2. The method of claim 1 for treating the dry eye syndrome with comprises forming said preparation by adding to said medication:
   0.2% by weight of hydroxypropylmethyl cellulose;
   0.11% by weight of potassium chloride;
   0.08% by weight of calcium chloride dihydrate; and
   0.02% by weight of magnesium chloride heptahydrate.

3. The method of claim 1 which further comprises adding to said medication an anti-inflammatory agent.

4. The method of claim 1 which further comprises adding to said medication an ocular hypotensive agent.

5. The method of claim 1 which further comprises adding to said medication an additional antimicrobial agent selected from a group consisting of anti-bacterial, anti-fungal, and anti-viral agents.

6. The method of claim 1 which further comprises adding to said medication a polymeric wetting, film-forming and viscosity-modifying agent selected from a group consisting of a substituted cellulose ether in a concentration range of 0.1% to 0.5% per weight, povidone in a concentration range of 0.1% to 5% by weight, and acrylic copolymers in a concentration range of 0.1% to 0.5% by weight.

* * * * *